United States Patent
Abt (10) Patent No.: US 12,324,605 B2
(45) Date of Patent: Jun. 10, 2025

(54) FORCE FIT EYE CANNULA WITH AUGMENTED SURFACE

(71) Applicant: Alcon Inc., Fribourg (CH)

(72) Inventor: Niels Alexander Abt, Winterthur (CH)

(73) Assignee: Alcon Inc., Fribourg (CH)

( * ) Notice: Subject to any disclaimer, the term of this patent is extended or adjusted under 35 U.S.C. 154(b) by 761 days.

(21) Appl. No.: 17/082,426

(22) Filed: Oct. 28, 2020

(65) Prior Publication Data
US 2021/0128195 A1    May 6, 2021

Related U.S. Application Data

(60) Provisional application No. 62/929,229, filed on Nov. 1, 2019.

(51) Int. Cl.
*A61B 17/34* (2006.01)
*A61F 9/007* (2006.01)

(52) U.S. Cl.
CPC ...... *A61B 17/3423* (2013.01); *A61F 9/00763* (2013.01); *A61B 2017/3458* (2013.01)

(58) Field of Classification Search
CPC ........ A61B 2017/3458; A61B 17/3423; A61B 17/3421; A61F 9/00736; A61F 9/00754; A61F 9/00763; A61F 9/007
See application file for complete search history.

(56) References Cited

U.S. PATENT DOCUMENTS

| | | |
|---|---|---|
| 6,146,387 A | 11/2000 | Trott et al. |
| 8,062,260 B2 | 11/2011 | Mccawley |
| 8,287,560 B2 | 10/2012 | Spaide |
| 8,298,188 B2 | 10/2012 | Okoniewski |
| 8,679,064 B2 | 3/2014 | Lopez |
| 9,320,534 B2 | 4/2016 | Vezzu |
| 10,039,565 B2 | 8/2018 | Vezzu |
| 10,864,001 B2 | 12/2020 | Vezzu |
| 10,905,462 B2 | 2/2021 | Ochoa |
| 2004/0073231 A1 | 4/2004 | Juan |
| 2008/0097346 A1 | 4/2008 | Charles |
| 2008/0172009 A1 | 7/2008 | Attinger |
| 2008/0177239 A1 | 7/2008 | Li |
| 2009/0326461 A1* | 12/2009 | Gresham ............ A61B 17/3421 604/167.03 |
| 2012/0207564 A1* | 8/2012 | Kochheiser ......... F16B 25/0084 29/525.12 |
| 2015/0238355 A1 | 8/2015 | Vezzu |
| 2016/0106461 A1* | 4/2016 | Morris ............... A61F 9/00736 600/204 |
| 2016/0296221 A1 | 10/2016 | Morris |

(Continued)

FOREIGN PATENT DOCUMENTS

| | | |
|---|---|---|
| EP | 2392274 A1 | 12/2011 |
| EP | 2392274 B1 | 7/2019 |

(Continued)

*Primary Examiner* — Deanna K Hall
(74) *Attorney, Agent, or Firm* — Patterson + Sheridan, LLP (57) ABSTRACT

A cannula with an augmented frictional surface to enhance physical security thereof. The augmented surface may be of unique morphology with rows or ribs. The ribs may be continuous or individual projections. They may be horizontal or screw-like. In one embodiment of screw-like ribs, rotations during placement and removal of the cannula may be employed.

13 Claims, 6 Drawing Sheets

(56) References Cited

U.S. PATENT DOCUMENTS

2018/0021061 A1  1/2018  Reid
2018/0103972 A1  4/2018  Grueebler et al.
2020/0337901 A1  10/2020  Charles

FOREIGN PATENT DOCUMENTS

WO   2015038725 A1   3/2015
WO   2015184173 A1   12/2015

* cited by examiner

FORCE FIT EYE CANNULA WITH AUGMENTED SURFACE

PRIORITY CLAIM

This application claims the benefit of priority of U.S. Provisional Patent Application Ser. No. 62/929,229 titled "FORCE FIT EYE CANNULA WITH AUGMENTED SURFACE," filed on Nov. 1, 2019, whose inventor is Niels Alexander Abt, which is hereby incorporated by reference in its entirety as though fully and completely set forth herein.

BACKGROUND

Over the years, many dramatic advancements in the field of eye surgery have taken place. One of the more common eye surgery procedures is a vitrectomy. Vitrectomy is the removal of some or all of the vitreous humor from a patient's eye. In some cases, where the surgery is limited to removal of clouded vitreous humor, the vitrectomy may constitute the majority of the procedure. However, a vitrectomy may accompany cataract surgery, surgery to repair a retina, to address a macular pucker, or a host of other issues.

Regardless of the particulars, a few different incisions will usually be required for most eye surgeries. For example, one incision may be made to provide access for a light instrument to illuminate the surgery. Another incision may be made for the vitrectomy probe or other surgical instrument. In the specific case of a vitrectomy, still another corresponding incision may be used to supply infusion fluid and maintain a proper balance within the eye in light of the withdrawn vitreous humor via the vitrectomy probe.

For each of these incisions, a cannula and trocar assembly may be used to make the incision and subsequently support the corresponding tool. That is, the assembly may be used to puncture the eye at the appropriate location, forming the incision. The centrally located internal trocar may then be removed from the assembly, leaving behind a tubular cannula that serves as a supportive port into the patient's eye.

For modern eye surgery, one sought after benefit is that these incisions ultimately be "suture-less". That is, following the procedure, removal of the cannulas leaves behind a wound so small that it might heal without the need for any sutures. As a practical matter, this has resulted in cannulas that are generally smaller than a millimeter in outer diameter with an even smaller lumen or internal diameter. Modern surgical tools are similarly designed to match and fit through the cannula for the procedure. Along these lines, note the fact that the end of a vitrectomy probe is referred to as a "needle". Indeed, in terms of dimensions, it is quite similar to a hypodermic.

In order to further increase the likelihood of cannula wounds remaining suture-less, an added surgical technique is generally employed. This technique involves inserting the cannula and trocar assembly at an angle instead of perpendicularly straight into the eye. Following surgery, this angled approach leaves behind a greater healing surface interface allowing for the tissue to be self-sealing to a degree.

Once the angled cannula is placed and the trocar removed, the surgeon may reposition the cannula to more of a perpendicular position. When the surgeon manually repositions the cannula as noted, there may be an increased likelihood of the cannula becoming dislodged from the eye. If this happens, the surgeon may need to replace the cannula and the patient may take on one more wound for the surgery.

In order to decrease the likelihood of the cannula becoming dislodged, some cannulas are produced with a tab or hump feature. This is a bump-like projection that emerges from the outer surface of the cannula at a location below the port end of the cannula that is accessible to the surgeon. In theory, the eye structure between this hump and the enlarged outer diameter port structure may remain somewhat wedged and secure. However, an improved retention feature is needed.

SUMMARY

A cannula to support a surgical procedure in a body of a patient is provided. The cannula is a force fit cannula with an outer surface configured with an augmentation for the force fit of the cannula relative the body. The augmentation includes a plurality of circumferential ribs to enhance a coefficient of friction at the outer surface.

DETAILED DESCRIPTION

In the following description, numerous details are set forth to provide an understanding of the present disclosure. However, it will be understood by those skilled in the art that the embodiments described may be practiced without these particular details. Further, numerous variations or modifications may be employed which remain contemplated by the embodiments as specifically described.

Embodiments are described with reference to certain types of vitrectomy surgical procedures. For example, a procedure in which vitreous humor is removed to address different eye conditions is illustrated. For such a procedure, embodiments of augmented surface force fit cannulas may be utilized at various locations. For example, such a cannula may facilitate positioning for a needle of a vitreous probe, a light source or an infusing instrument. Such procedures may be utilized to address retinal detachments, macular pucker, macular holes, vitreous floaters, diabetic retinopathy or a variety of other eye conditions. The interventional tools for eye surgery may each be supported by an augmented surface force fit cannula.

Figure 1:
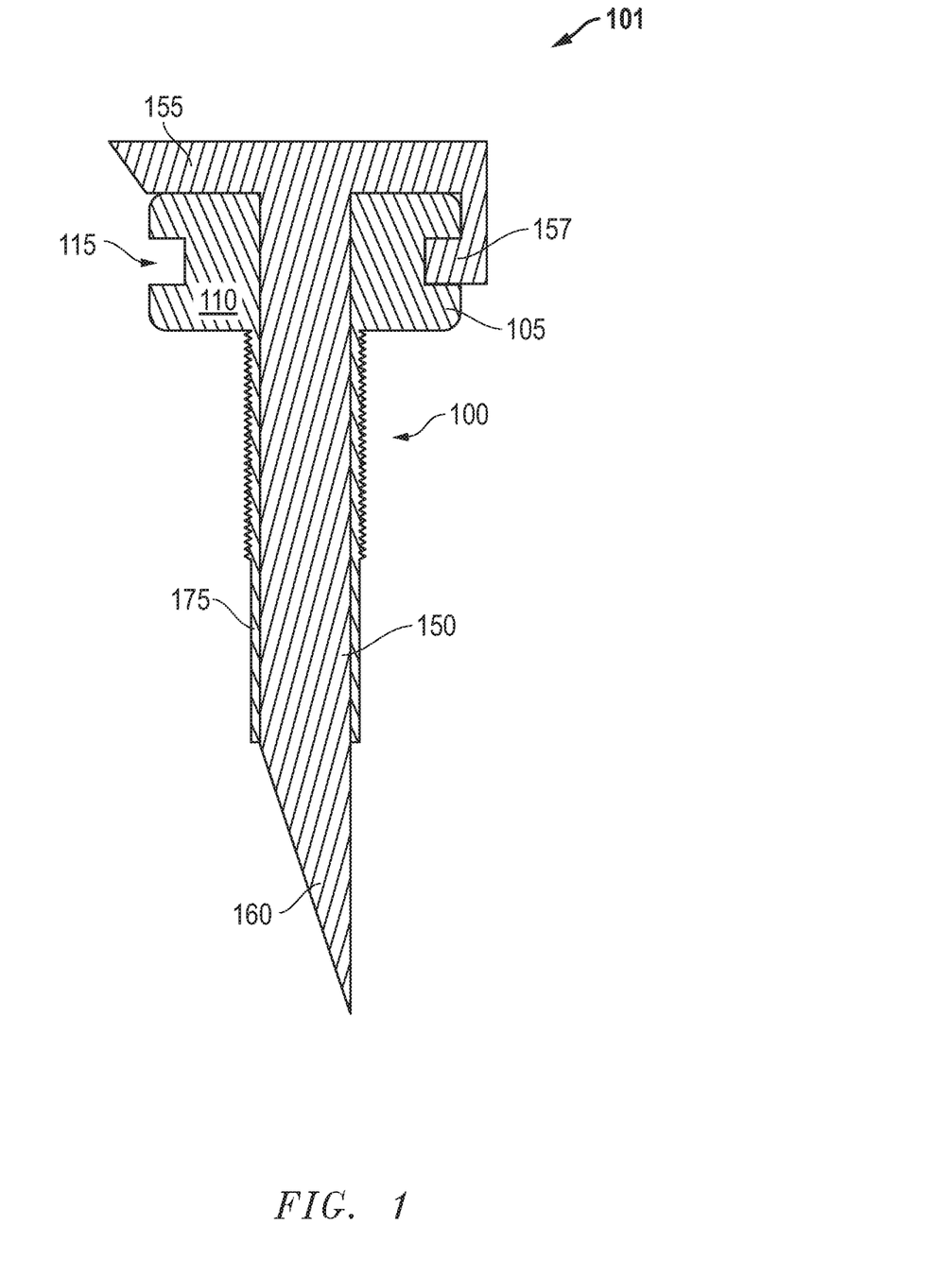
FIG. 1 is a side cross-sectional view of a trocar 101 with an embodiment of an augmented surface force fit cannula.

Referring now to FIG. 1, a side cross-sectional view of a trocar 101 with an embodiment of an augmented surface force fit cannula 110 is shown. Specifically, the trocar 101 is an assembly that includes a trocar 150 that is configured to penetrate tissue such as eye tissue. Thus, the entire assembly 101 may be inserted into the tissue, including the cannula 110. As a result, removal of the trocar 150 following the insertion of the trocar assembly 101 leaves behind the force fit cannula 110 to serve as a structural port for guided surgical access to or beyond the tissue (e.g. see FIG. 2).

Continuing with reference to FIG. 1, the trocar 150 includes a blade end 160 for penetrating tissue as noted above. The degree of sharpness at this end 160 may vary depending upon the application. The central portion of the trocar leads to a head 155 that is manually accessible to the surgeon. Thus, following positioning of the assembly 101, a tab 157 may be displaced from a key recess 115 at the head 105 of the cannula 110. In this way, the trocar 150 may be removed from the remainder of the assembly 101. This leaves behind a tubular port 175 to provide the noted guided surgical access as illustrated in FIG. 2.

Continuing with FIG. 1, with added reference to FIG. 2, the placed cannula 110 may be below a millimeter in diameter with an internal lumen gauge of 23, 25 or 27 (e.g. between about 0.40 mm and about 0.65 mm) (other dimensions are also contemplated). Once more, at the outset of surgery, and later over the course of the surgery, the cannula 110 is likely to be moved in a pivoting or angling type of manner for sake of accommodating surgical instruments therethrough. Thus, the risk of dislodging the cannula 110 exists. Therefore, the outer surface of the cannula includes an augmented surface region 100 to introduce a degree of frictional resistance to such a dislodging. In the embodiment shown, this region 100 is located immediately below the cannula head 105 for aligning with eye tissue (e.g. see the sclera 270 also depicted at FIGS. 3A, 3B and FIG. 4). Of course, the region 100 may extend beyond the location immediately below the cannula head 105. In one embodiment, the augmented surface region 100 covers the substantial entirety of the outer surface of the tubular port 175. Alternatively, the region 100 may be limited to a predetermined distance below the cannula head 110.

Figure 2:
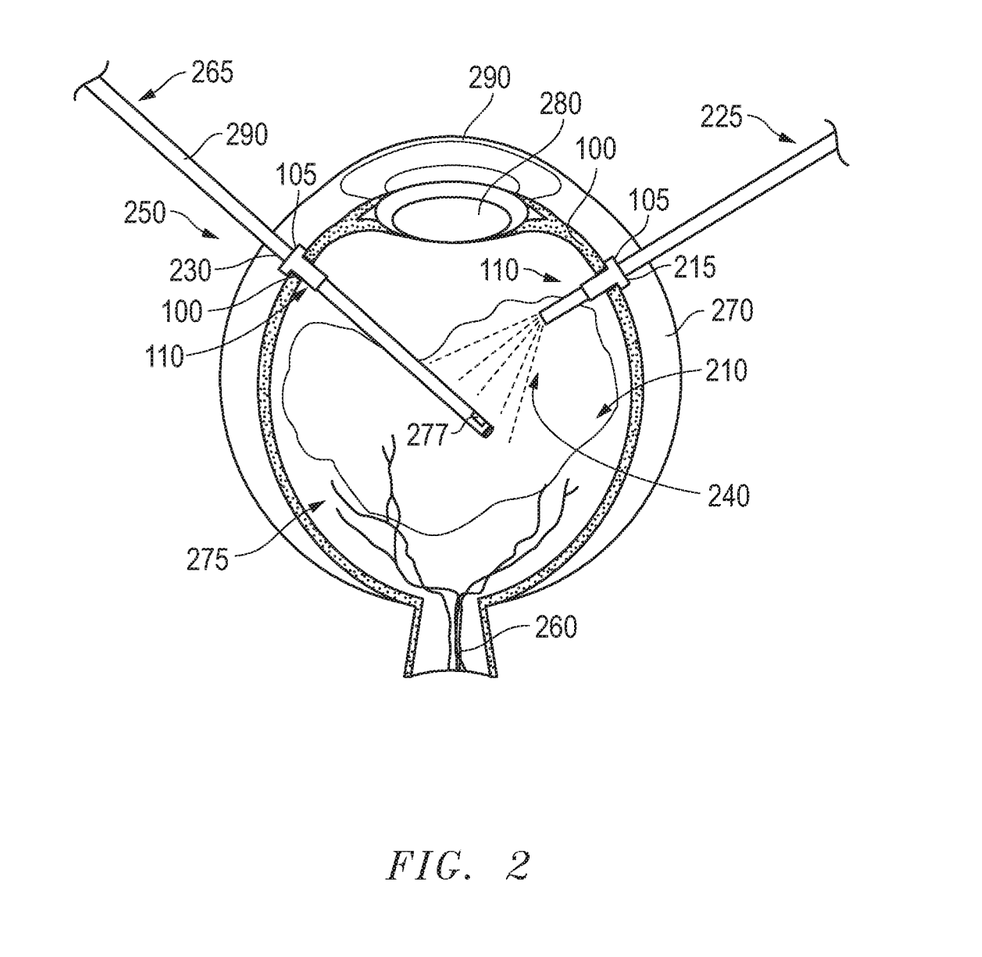
FIG. 2 is a side cross-sectional overview of a patient's eye during a vitrectomy procedure in which the force fit cannula of FIG. 1 is utilized.

Referring specifically now to FIG. 2, a side cross-sectional overview of a patient's eye 250 is illustrated during a vitrectomy procedure in which the force fit cannula 110 of FIG. 1 is utilized. More specifically, two such cannulas 110 are shown placed to facilitate guided support to a vitrectomy probe 265 and a light source 225. The cannulas 110 are not only small in diameter as noted above but also may be relatively short in length along with the rest of the trocar 101 of FIG. 1. This helps avoid risk of damage to the optic nerve 260, retina 275 and other more delicate features at the back of the eye 250. Further, the augmented surface region 100 provides a substantial frictional resistance to dislodging at the interface 300 between the region 100 and adjacent eye tissue 270 (see FIGS. 3A and 3B).

With the region 100 present at the surface of each cannula 110, they may be safely and securely moved to a relatively perpendicular position for receiving of instruments 265, 225 as noted above. That is, as detailed below, an enhanced friction interface may reduce the possibility of accidental cannula removal. In the illustrated example, the needle 290 of a vitrectomy probe 265 is inserted through one of the cannulas 110 and directed toward a region 210 where vitreous humor is to be removed. Specifically, as described above, a suction is applied and the port 277 is used for the uptake of the vitreous humor or other substances. For example, in the procedure illustrated, a hemorrhage may be taking place in the region 210 such that blood is drawn into the port 277 along with the vitreous humor.

The surgery illustrated also includes a light instrument 225 reaching into the eye 250 through another cannula 110. In both cases, the cannulas 110 are positioned in an offset manner at the sclera 270. In this way, the more delicate cornea 290 and lens 280 may be avoided.

Figure 3A:
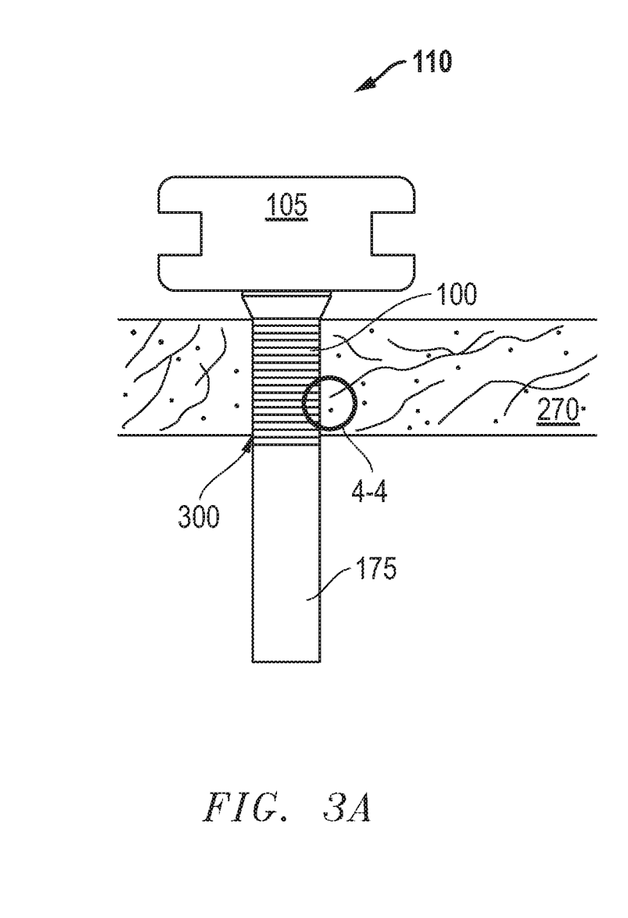
FIG. 3A is a side partially sectional view of one embodiment of the cannula in the eye of FIG. 2.
Figure 3B:
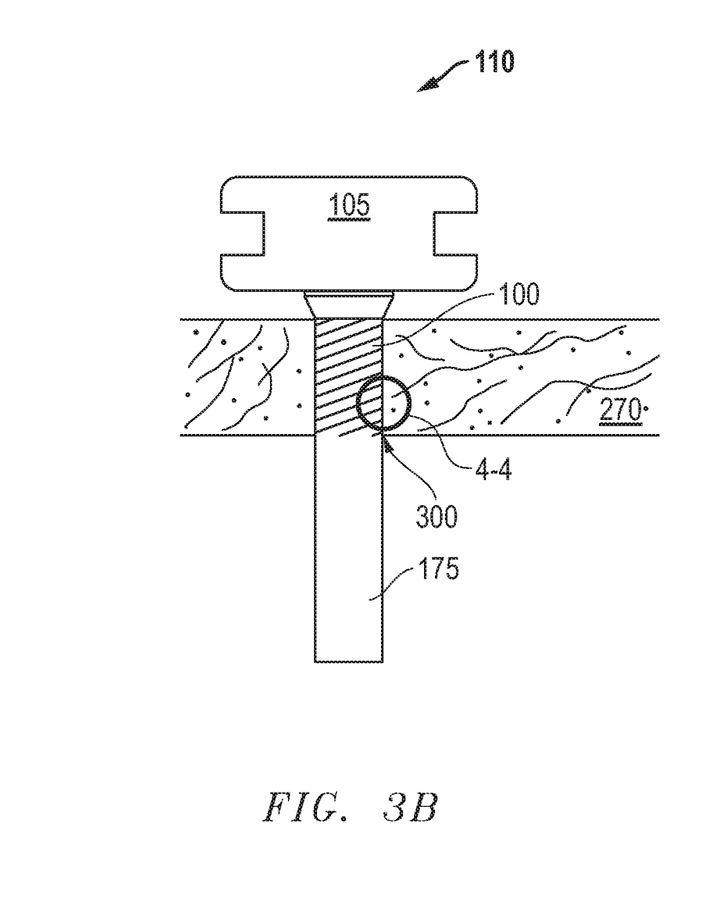
FIG. 3B is a side partially sectional view of another embodiment of the cannula in the eye of FIG. 2.

Referring now to FIGS. 3A and 3B, side partially sectional views of different embodiments of the cannula 110 are shown positioned in the eye of FIG. 2. More specifically, the augmented surface region 100 may be made up of horizontal rows of ribs as illustrated in FIG. 3A or presented in more of a screw-type configuration as illustrated in FIG. 3B. With specific reference to either embodiment, it is apparent how a slip or pull on either cannula 110 would face resistance due to the illustrated rows that project from the region 100 at the tubular port 175. That is, with the port 175 tightly surrounded by the sclera tissue 270, the projection rows of the region 100 would result in frictional resistance to such a pull, helping the cannulas 110 to remain in place.

For the embodiment of FIG. 3B, to minimize injury, the entire trocar assembly 101 of FIG. 1 may penetrate the sclera 270 with the cannula 110 being rotated to a degree in a given direction. With specific reference to the embodiment illustrated, this would be a clockwise direction due to the angle of the threads at the region 100. In this way, the cannula 110 may screw into the sclera 270 to a certain degree so as to minimize injury. Similarly, following surgery, the cannula 110 may be rotated in an opposite direction during removal, again to help minimize injury (e.g. counterclockwise for the illustrated embodiment). Note that strategically rotating the cannula 110 in one direction or another at the appropriate time of placement or removal may reduce the frictional resistance to the placement or removal. However, during surgery, cannula movements that are of concern for potential dislodging are not strategically rotational. Therefore, the risk of losing frictional resistance to dislodging is not of any practical concern for such an embodiment.

Figure 4:
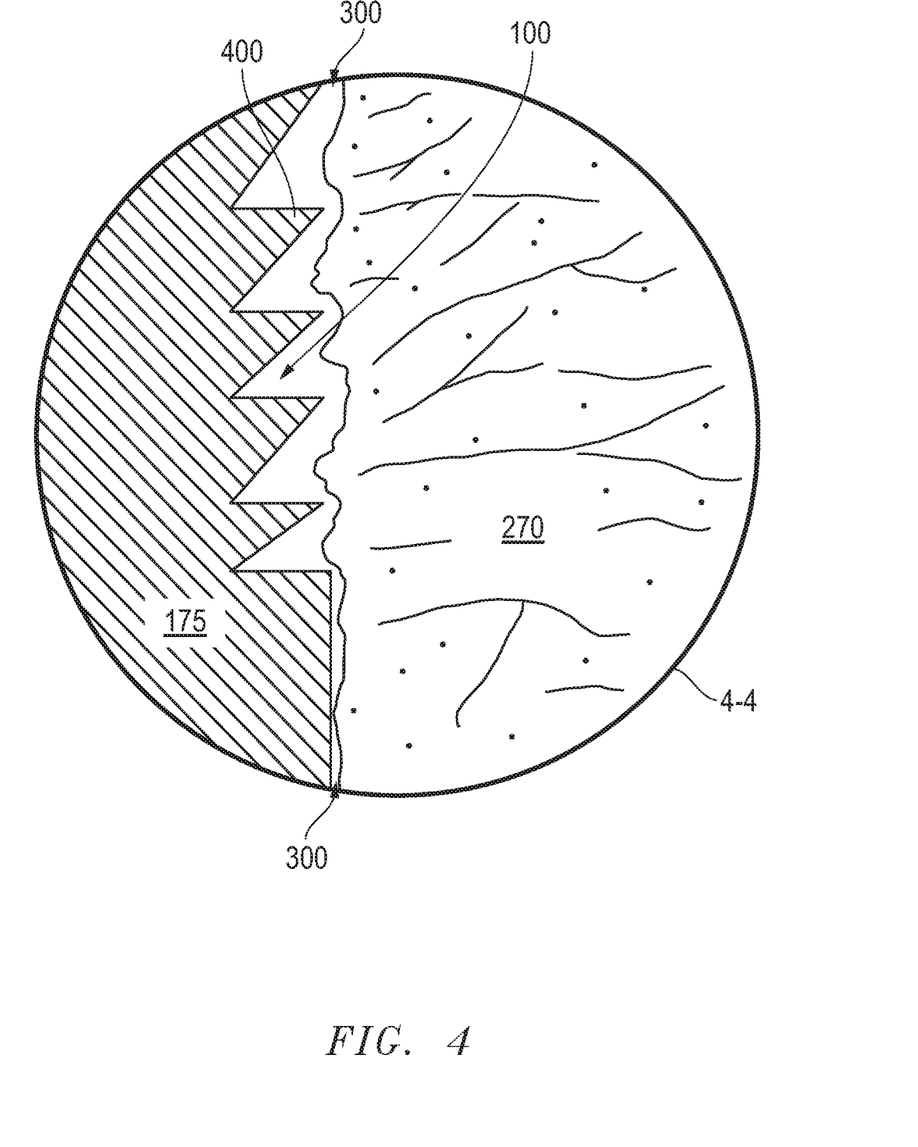
FIG. 4 is an enlarged view of an interface between the cannula and eye tissue taken from 4-4 of FIGS. 3A and 3B.

Referring now to FIG. 4, an enlarged view of an interface 300 is shown taken from 4-4 of FIGS. 3A and 3B. The interface 300 is between the cannula 100 at the augmented surface region 100 of the port structure 175 and eye tissue 270. Note that in this particular illustration, the port structure and surface region 100 are shown in cross section right at the interface 300. Thus, the surface region 100 could be either of the embodiments of FIG. 3A or 3B. That is, the individual ribs or projections 400 may either be horizontal or screw-like in nature.

Indeed, a variety of additional morphologies are also possible. For example, the projections 400 may be continuous ribs or made up of rows of individual scale or teeth-like structures presenting a frictional grid to the adjacent tissue 270. Once more, the depicted projections 400 emerge perpendicularly or horizontally from the port structure 175 for a distance/height of about 25 microns (other dimensions are also possible, for example, the distance/height may be approximately in a range of 5 to 10 microns high). However, this is not required and in one embodiment, the projections 400 may be angled upward such that insertion is even more favored over dislodging relative the surrounding tissue 270.

Figure 5A:
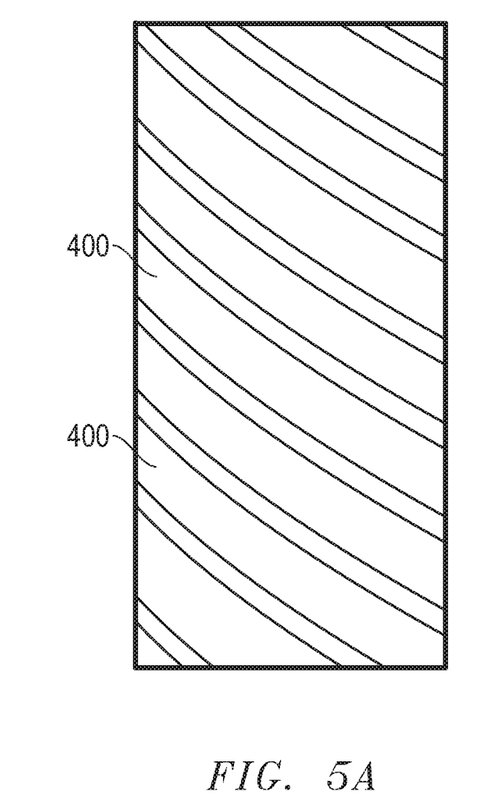
FIG. 5A is a view of an attenuated surface of the force fit cannula of FIG. 1 revealing individual projection rows thereat.
Figure 5B:
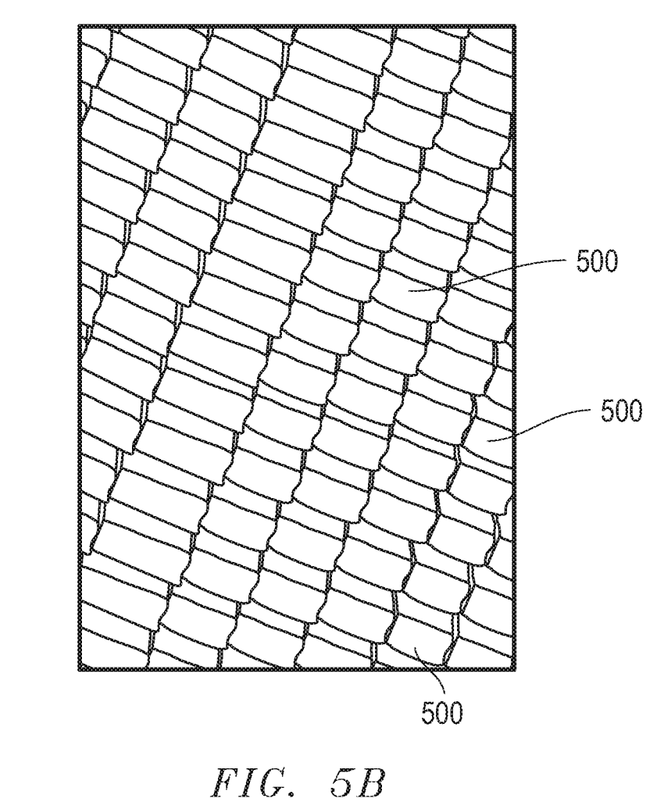
FIG. 5B is another view of the attenuated surface of the force fit cannula revealing individual projections forming the rows of FIG. 5A.

Referring now to FIGS. 5A and 5B, closer views of embodiments of the augmented surface region 100 are shown such as might be apparent via a scanning electron microscope (SEM). Specifically, FIG. 5A illustrates how projections 400 in rows as illustrated in FIGS. 3A and 4 might appear. Alternatively, FIG. 5B illustrates individual teeth-like projections 500 as referred to above that might present a frictional grid surface to adjacent tissue 270 as shown in FIG. 4. In the embodiment of FIG. 5B, these projections 500 are roughly 10×10 to 50×50 micron with about 5-25 micron depth (other dimensions for the projections are also contemplated (e.g., approximately in a range of 5 to 10 microns Further, notice that although presented as individual teeth, the projections 500 are aligned in rows similar to that of FIG. 4.

Figure 6:
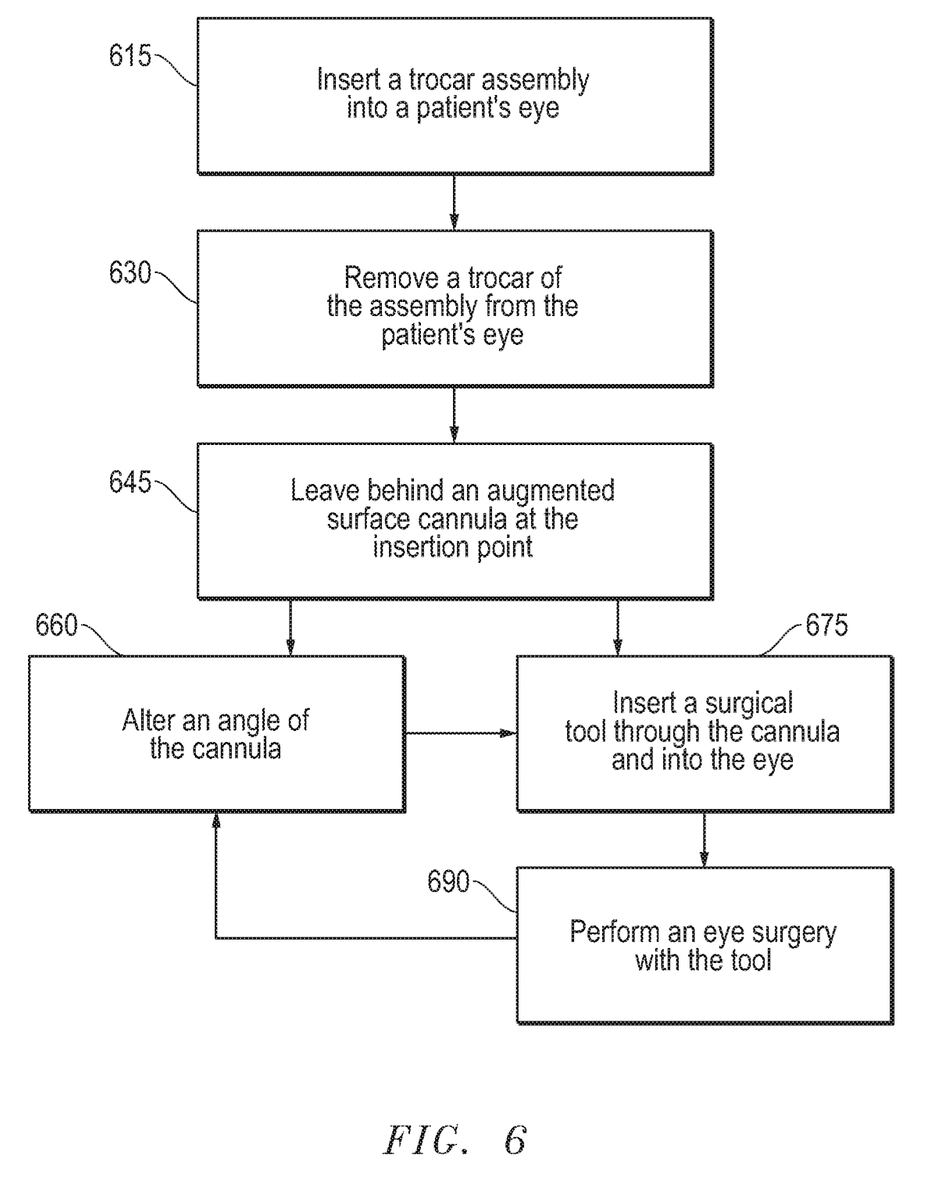
FIG. 6 is a flow-chart summarizing an embodiment of utilizing a force fit cannula with augmented surface to support eye surgery.

Referring now to FIG. 6, a flow-chart summarizing an embodiment of utilizing a force fit cannula with augmented surface to support eye surgery is shown. Specifically, a trocar assembly is inserted into a patient's eye as indicated at 615 with the inner trocar of the assembly removed as indicated at 630. Thus, a uniquely secure augmented surface cannula is left behind at the insertion point (see 645).

As indicated at 660, 675 and 690, the cannula may have its angle repeatedly altered, a surgical tool placed therethrough and even support ongoing surgery with the tool. Indeed, these things may all occur repeatedly and in various sequence throughout the surgery, including prior to surgery with the cannula placement. Nevertheless, the force fit cannula is uniquely configured with an augmented surface region for enhanced frictional capacity relative to adjacent tissue. Thus, in spite of all of the noted movements, the possibility of cannula dislodging is reduced.

Embodiments described hereinabove include cannulas that enhance retention during and following placement for a surgical procedure. Additionally, the unique morphology is such that the placement avoids the introduction of stretching forces that might add to injury. Ultimately, a more water tight and secure surgical support is provided.

The preceding description has been presented with reference to presently described embodiments. However, other embodiments and/or features of the embodiments disclosed but not detailed hereinabove may be employed. Furthermore, persons skilled in the art and technology to which these embodiments pertain will appreciate that still other alterations and changes in the described structures and methods of operation may be practiced without meaningfully departing from the principle and scope of these embodiments. Additionally, the foregoing description should not be read as pertaining only to the precise structures described and shown in the accompanying drawings, but rather should be read as consistent with and as support for the following claims, which are to have their fullest and fairest scope.

I claim:

1. A cannula to support a surgical procedure in a body of a patient, the cannula comprising:
an outer surface configured with an augmentation region for enhanced frictional resistance to dislodging of the cannula from the body, wherein:
the augmentation region comprises a plurality of individual horizontal rows,
each of the plurality of individual horizontal rows is arranged along a plane perpendicular to a major axis of the cannula;
each of the plurality of individual horizontal rows comprises a plurality of projections extending from the outer surface, and
the projections comprise teeth-like structures.

2. The cannula of claim 1, wherein the cannula is a force fit cannula and the surgical procedure is an eye surgery.

3. The cannula of claim 1, further comprising:
a head;
a tubular port coupled to the head, the tubular port to accommodate the augmentation region and penetrate the body of the patient during the procedure.

4. The cannula of claim 3, wherein the tubular port includes a lumen inner diameter of between about 0.40 millimeters (mm) and about 0.65 mm.

5. The cannula of claim 3, wherein the augmentation region occupies a substantial entirety of an outer surface of the tubular port from the head to a distal end of the tubular port.

6. A trocar assembly, comprising:
a trocar with a blade for penetrating a body of a patient; and
a cannula configured to be disposed about the trocar to support a surgical procedure directed at the body upon removal of the trocar, the cannula comprising an outer surface configured with an augmentation region for enhanced frictional resistance to dislodging of the cannula from the body, wherein:
the augmentation region comprises a plurality of individual horizontal rows,
each of the plurality of individual horizontal rows is arranged along a plane perpendicular to a major axis of the cannula;
each of the plurality of individual horizontal rows comprises a plurality of projections extending from the outer surface, and
the projections comprise teeth-like structures.

7. The trocar assembly of claim 6, wherein the cannula further comprises a tubular port to accommodate the augmentation region at an outer surface thereof.

8. The trocar assembly of claim 6, wherein the individual horizontal rows of projections present a frictional grid at an interface of the augmentation region and the body of the patient.

9. The trocar assembly of claim 8, wherein each projection in the frictional grid has lateral dimensions between 10 micron by 10 micron to 50 micron by 50 micron and a depth between 5 micron to 25 micron.

10. A method comprising:
placing a cannula in a patient's eye; and
enhancing frictional resistance to dislodging of the cannula from the patient's eye with an outer surface of the cannula configured with an augmentation region, wherein:
the augmentation region comprises a plurality of individual horizontal rows,
each of the plurality of individual horizontal rows is arranged along a plane perpendicular to a major axis of the cannula;
each of the plurality of individual horizontal rows comprises a plurality of projections extending from the outer surface, and
the projections comprise teeth-like structures.

11. The method of claim 10, further comprising:
altering an angle of the cannula in the eye after the placing; and
enhancing frictional resistance to dislodging with the augmentation region during the altering.

12. The method of claim 10, further comprising:
removing a trocar from an internal lumen of the cannula;
inserting a surgical tool through the cannula into the eye;
performing an eye surgery with the tool; and
enhancing frictional resistance to dislodging with the augmentation region during the removing, inserting and performing.

13. The method of claim 12, wherein the eye surgery is a vitrectomy.

\* \* \* \* \*